(12) United States Patent
Eyssler

(10) Patent No.: US 9,678,028 B2
(45) Date of Patent: Jun. 13, 2017

(54) METHOD AND DEVICE FOR DETERMINING AN INSULATION VARIABLE

(71) Applicant: Lisa Draexlmaier GmbH, Vilsbiburg (DE)

(72) Inventor: Gernot Eyssler, Altfraunhofen (DE)

(73) Assignee: Lisa Draexlmaier GmbH, Vilsbiburg (DE)

( * ) Notice: Subject to any disclaimer, the term of this patent is extended or adjusted under 35 U.S.C. 154(b) by 11 days.

(21) Appl. No.: 15/005,296

(22) Filed: Jan. 25, 2016

(65) Prior Publication Data

US 2016/0216220 A1    Jul. 28, 2016

(30) Foreign Application Priority Data

Jan. 26, 2015 (DE) .................. 10 2015 101 074

(51) Int. Cl.
*H01H 31/12*  (2006.01)
*G01N 27/416*  (2006.01)
*G01N 27/04*  (2006.01)
*G01R 27/02*  (2006.01)
*G01R 31/36*  (2006.01)

(52) U.S. Cl.
CPC .......... *G01N 27/04* (2013.01); *G01N 27/416* (2013.01); *G01R 27/025* (2013.01); *G01R 31/3662* (2013.01); *G01R 31/3606* (2013.01); *G01R 31/3627* (2013.01)

(58) Field of Classification Search
CPC .. G01N 27/04; G01N 27/416; G01R 31/3662; G01R 31/3627; G01R 27/025
USPC .................................................. 324/551, 430
See application file for complete search history.

(56) References Cited

U.S. PATENT DOCUMENTS

| 2008/0224687 | A1 | 9/2008 | Breese et al. | |
| 2012/0016613 | A1* | 1/2012 | Yang ..................... | G01R 27/16 702/65 |
| 2013/0314097 | A1* | 11/2013 | Hausberger ........... | B60L 3/0069 324/503 |
| 2015/0042350 | A1* | 2/2015 | Bober ................ | G01R 31/3627 324/430 |

FOREIGN PATENT DOCUMENTS

| DE | 196 18 897 B4 | 4/2006 |
| DE | 10 2008 013 436 A1 | 11/2008 |
| WO | WO 2011/160881 A1 | 12/2001 |

\* cited by examiner

*Primary Examiner* — Amy He
(74) *Attorney, Agent, or Firm* — Finnegan, Henderson, Farabow, Garrett & Dunner, LLP

(57) ABSTRACT

A method and device for determining an insulation variable of a network. The method may comprise measuring a first voltage at the network, connecting the auxiliary system to the network, measuring a second voltage at the network, disconnecting the auxiliary system from the network, measuring a third voltage at the network, and determining the insulation variable based on the first voltage, the second voltage, and the third voltage.

20 Claims, 2 Drawing Sheets

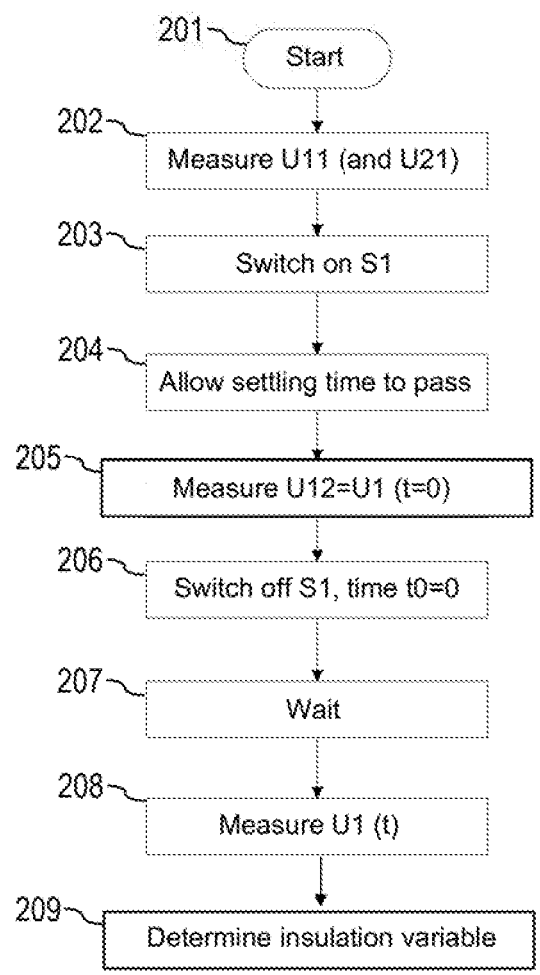

METHOD AND DEVICE FOR DETERMINING AN INSULATION VARIABLE

CROSS REFERENCE TO RELATED APPLICATION

This application is based upon and claims the benefit of prior German Patent Application No. 10 2015 101 074.7, filed on Jan. 26, 2015, the entire contents of which are incorporated herein by reference.

TECHNICAL FIELD

The present disclosure relates to a method and device for determining an insulation variable of a network, such as an insulation resistance of a battery, which may operate in the high-voltage range.

BACKGROUND OF THE DISCLOSURE

For safety reasons, it is important to determine insulation resistances with respect to high-voltage devices.

WIPO Patent Application No. 2011/160881 A1 describes a method for determining the insulation resistance of an ungrounded electrical network, in which a measuring voltage may be fed into the network via a voltage divider. A measuring current flowing after applying the measuring voltage is measured during at least three different time intervals during a transient period of the network. The insulation resistance may be determined based on the measurement results. However, the method requires a high component complexity and includes a variety of drawbacks. For example, it is only possible to determine the overall insulation resistance, and partial insulation resistances cannot be determined.

German Patent Application No. 196 18 897 B4 describes a circuit for determining the insulation resistance of a battery (such as a rechargeable battery) in stand-alone operation. The circuit may determine the insulation resistance by measuring an open-circuit voltage and a load voltage, wherein a series connection of two capacitors may be connected to the battery terminals for storing the voltage values during the measurement, and the shared point of the capacitors may connect to a bleeder resistor. However, this requires long measuring times for large insulation capacitances.

SUMMARY

Embodiments of the present disclosure provide a method and device for efficiently determining an insulation resistance of a battery in the high-voltage range.

According to embodiments of the present disclosure, a method for determining an insulation variable of a network is disclosed, wherein a measuring system, also referred to herein as an auxiliary system, may be temporarily connected to the network and a reference point, the method comprising: measuring a first voltage at the network when the measuring system is not connected to the network; connecting the measuring system to the network; measuring a second voltage at the network; disconnecting the measuring system from the network; measuring a third voltage at the network; and determining an insulation variable based on the first voltage, the second voltage, and the third voltage.

Embodiments of the present disclosure may enable determining the insulation measurement at reduced cost and material expenditure. Furthermore, the duration of the insulation measurement may be reduced.

In some embodiments, the second voltage and third voltage may be measured as voltages that drop at the measuring system. The first voltage may be determined between the network and the reference point. The measuring system may be an auxiliary circuit or an auxiliary system.

According to embodiments of the present disclosure, a processing unit may carry out the voltage measurements. For example, the processing unit may control the measuring system to temporarily connect to the network. The measuring system may disconnect from the network, for example, by intermittently interrupting a connection between the network and the measuring system.

In some embodiments, the reference point may be ground. Ground may correspond to a connection to a car body or to another reference potential in a vehicle.

In some embodiments, the insulation variable is an insulation capacitance or an insulation resistance.

In some embodiments, the network is an electrical supply network. For example, the network may be an electrical supply network of a motor vehicle. The network may comprise at least one DC voltage source, such as a battery.

In some embodiments, the measuring system may temporarily connect to the network, between a supply terminal of the network and the reference point (such as ground), using a switch. The switch may be an electronic or a mechanical switch.

In some embodiments, the measuring system may comprise a capacitor, a first resistor, and a switch connected in series, and a second resistor connected in parallel to the capacitor.

In some embodiments, a predefined settling time is allowed to pass after the measuring system is connected to the network, and before the second voltage is measured. This settling time may be determined by a time constant $\tau$ (RC circuit) from the first resistor and the capacitor of the measuring system, which are connected in series. The time during which the measuring system is connected to the network may be shorter than the time constant $\tau$.

In some embodiments, a predefined duration is allowed to pass after the measuring system is disconnected from the network, and before the third voltage is measured.

In some embodiments, a parallel insulation resistance RP, equal to the values of insulation resistances R1 and R2 connected in parallel, is measured as the insulation variable in accordance with $$RP = \frac{-t1}{CP \cdot \ln\left(1 - \frac{U1(t1) - U12}{U11 - U12}\right)}$$

wherein CP is a parallel insulation capacitance equal to the values of insulation capacitors C1 and C2 connected in parallel, and measured in accordance with $$CP = Cm * \frac{U12}{U11 - U12}$$

wherein
RP is the parallel insulation resistance,
CP is the parallel insulation capacitance,
U11 is the first voltage,
U12 is the second voltage, U1(t1) is the third voltage,
t1 is the predefined duration before the third voltage is measured, and
Cm is the capacitor in the measuring system.

According to embodiments of the present disclosure, a fourth voltage may be measured before the measuring system is connected to the network. The fourth voltage is measured between the reference point and a supply terminal of the network that is not used for measuring the second voltage. Insulation resistances R1 and R2 of the network are determined in accordance with $$R1 = RP \cdot \left(1 - \frac{U11}{U21}\right)$$

and $$R2 = \frac{-R1 \cdot U11}{U21}$$

wherein
R1 is an insulation resistance in parallel to the measuring system,
R2 is an insulation resistance at which the fourth voltage drops, and
U21 is the fourth voltage.

In some embodiments, the duration t1 depends on a resolution of an analog-to-digital converter connected to the measuring system.

In some embodiments, a device for determining an insulation variable of a network is disclosed. The device may comprise a measuring system and a processing unit, wherein the measuring system may be temporarily connected to the network and a reference point, and wherein the processing unit is configured to perform the following operations: measuring a first voltage at the network when the measuring system is not connected to the network; connecting the measuring system to the network; measuring a second voltage at the network; disconnecting the measuring system from the network; measuring a third voltage at the network; and determining an insulation variable based on at least one element of the measuring system, the first voltage, the second voltage, and the third voltage.

In some embodiments, the measuring system and processing unit may be implemented in a shared component or unit. For example, the measuring system may comprise a corresponding processing unit, or the processing unit may comprise at least one of the measuring systems disclosed in the present disclosure.

In some embodiments, the device may be a circuit. The device may comprise hardware and/or software.

In some embodiments, a motor vehicle is disclosed, the motor vehicle comprising at least one device as described in the present disclosure.

Embodiments of the present disclosure may be used to determine an insulation measurement in a high-voltage system. Such a high-voltage system may comprise a battery, for example, which supplies a voltage of more than 50 V, or more than 100 V.

Descriptions in the present disclosure relating to a particular claim category, such as a method, apply correspondingly to all other claim categories disclosed herein.

The properties, features and advantages as described in the present disclosure, and the manner in which these are achieved, will become more apparent and understandable in connection with the following detailed description. The foregoing general description and the following detailed description are exemplary and explanatory only, and are not restrictive of embodiments consistent with the present disclosure. Further, the accompanying drawings illustrate embodiments of the present disclosure, and together with the description, serve to explain principles of the present disclosure. For clarity and illustrative purposes, identical or like-acting elements may be denoted by the same reference numerals.

BRIEF DESCRIPTION OF FIGURES

FIG. 2 shows an exemplary method for measuring an insulation resistance according to the present disclosure.

DETAILED DESCRIPTION

Figure 1:
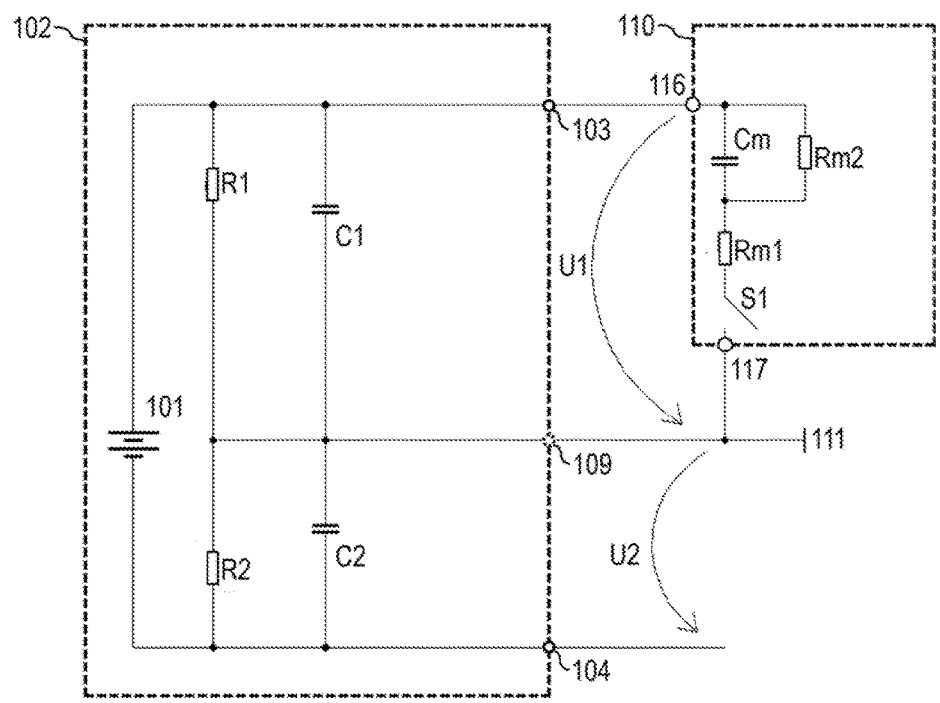
FIG. 1 shows an exemplary device for determining an insulation resistance of a battery according to the present disclosure.

According to embodiments of the present disclosure, an insulation resistance may be determined for a network or on a network. The network may comprise an energy source, such as a battery, which may be connected via electrical lines (such as multicore cables) to at least one consumer device. The battery may be a rechargeable battery. The network may be part of an autonomous system, such as an energy supply network in a vehicle.

According to embodiments of the present disclosure, a voltage is measured in at least one point of the network. A measuring system may be temporarily connected to the network. For example, the measuring system may be temporarily connected to the network for a predefined duration. The measuring system may include a circuit comprising at least one resistor and at least one capacitor. The measuring system may measure a change in voltage, and an insulation capacitance of the network may be determined based on the measured change in voltage. The measuring system may then be disconnected from the network, and an insulation resistance may be determined from a change in voltage that varies over time.

FIG. 1 shows an exemplary measuring system comprising a circuit 110 for determining at least one insulation resistance of a battery 101. The circuit 110 may be arranged between the battery 101 and ground 111. The battery 101 comprises two terminals 103 and 104, which are also referred to as poles of the battery, and to which at least one consumer device may be connected. The battery 101 may be designed as a high-voltage battery to supply a voltage of 100 V or more, for example.

As shown in FIG. 1, an exemplary circuit 102 comprises the battery 101, including terminals 103 and 104, two insulation resistors R1 and R2, and two insulation capacitors C1 and C2. The insulation resistors R1 and R2 may be connected in series to each other, and this series connection may be arranged in parallel to the battery 101. The insulation capacitor C1 may be arranged in parallel to the insulation resistance R1, and the insulation capacitor C2 may be arranged in parallel to the insulation resistance R2. The center tap of the series connection composed of the insulation resistances R1, R2 (and the insulation capacitors C1, C2) may be denoted as a node 109. Node 109 may be connected to ground 111 by way of, for example, the body of a motor vehicle, as the reference potential.

The circuit 110 may at least be temporarily connected to the battery 101 by being connected via terminal 116 to terminal 103, and via terminal 117 to ground 111. The circuit 110 may comprise a capacitor Cm, a resistor Rm1, a resistor Rm2, and a switch S1. The terminal 116 may be connected to terminal 117 via a series connection comprising the capacitor Cm, the resistor Rm1, and the switch S1. The resistor Rm2 may be connected in parallel to the capacitor Cm. Switch S1 may comprise an electronic switch, such as a transistor, or a mechanical switch or push-button. Switch S1 may be actuated by a control and/or calculation unit configured to record the measured values and calculate the insulation resistance.

As shown in FIG. 1, voltage U1 drops between terminal 103 and node 109, and a voltage U2 drops between node 109 and terminal 104.

FIG. 2 shows an exemplary method for measuring the insulation resistances R1 and R2. The following designations are used in describing the exemplary method shown in FIG. 2.

U11 denotes the voltage U1 at the time before switch S1 is closed.

U21 denotes the voltage U2 at the time before switch S1 is closed.

U1($t$) denotes the voltage U1 at the time after switch S1 has been closed and then re-opened.

U12 denotes the voltage U1 just before switch S1 is re-opened. The voltage U12 equals the voltage U1($t$=0) immediately after the switch S1 is re-opened.

In step 201, the measurement starts. This may take place prior to starting the vehicle, for example, to determine whether insulation resistances satisfy predetermined criteria before the vehicle starts.

In step 202, voltage U11 is measured. Optionally, voltage U21 may also be measured. However, if only the parallel circuit of the insulation resistances R1 and R2 is to be determined, the measurement of voltage U21 may not be required.

In step 203, switch S1 is closed.

In step 204, a predefined settling time is allowed to lapse. This settling time may be influenced by the time constant:

$$\tau = Rm1 \cdot Cm.$$

The time during which switch S1 is closed, however, may be shorter than time constant $\tau$. For example, time constant $\tau$ may be greater than the duration during which switch S1 is dosed by at least a factor of 2 or at least a factor of 10.

In step 205, voltage U12=U1($t$=0) is measured at time $t$=0.

In step 206, switch S1 is opened at time t0=0.

In step 207, a predefined settling time is allowed to lapse. The waiting period may correspond to the resolution of an analog to digital converter that is connected to the measuring system and takes the analog measured value of voltage U1, at three different times, and converts it to a digital value. For example, the higher the resolution of the converter, the shorter the waiting period may be, because a digital value may be determined for voltage U1 a short time after t0=0.

In step 208, voltage U1($t$) is measured.

In step 209, at least one insulation variable may be determined based on at least one of the calculations as described in the present disclosure.

A parallel insulation capacitance CP, equal to the values of insulation capacitors C1 and C2 connected in parallel, may be determined as follows:

$$CP = Cm * \frac{U12}{U11 - U12}$$

A parallel insulation resistance RP, equal to the values of insulation resistances R1 and R2 connected in parallel, may then be calculated using the following formula:

$$RP = \frac{-t1}{CP \cdot \ln\left(1 - \frac{U1(t1) - U12}{U11 - U12}\right)}$$

wherein time t1 corresponds to the time at which voltage U1($t$) is measured in step 208.

The individual insulation resistances may then be determined according to the following calculations:

$$R1 = RP \cdot \left(1 - \frac{U11}{U21}\right)$$

$$R2 = \frac{-R1 \cdot U11}{U21}$$

For illustrative purposes, an example for calculating an insulation variable is provided below.

Provided with illustrative the measured values

Cm=1 µF

U11=200V,

U12=134V, t1=0.1 s, and

U1($t1$)=140V,

CP may be calculated in accordance with:

$$C_P = C_m * \frac{U_{12}}{U_{11} - U_{12}}$$

$$= 1 \text{ µF} \cdot \frac{134 \text{ V}}{200 \text{ V} - 134 \text{ V}}$$

$$= 2 \text{ µF}$$

RP may then be calculated in accordance with:

$$R_P = \frac{-t_1}{C_P \ln\left(1 - \frac{U_1(t_1) - U_{12}}{U_{11} - U_{12}}\right)}$$

$$= \frac{-0.1 \text{ s}}{2 \text{ µF} * \ln\left(1 - \frac{140 \text{ V} - 134 \text{ V}}{200 \text{ V} - 134 \text{ V}}\right)}$$

$$= 500 \text{ k}\Omega$$

The individual insulation resistances R1 and R2 may then be determined according to the following calculations:

$$R_1 = R_P * \left(1 - \frac{U_{11}}{U_{21}}\right)$$

$$= 500 \text{ k}\Omega * \left(1 - \frac{200 \text{ V}}{-200}\right)$$

$$= 1 \text{ M}\Omega$$

and

-continued $$R_2 = \frac{-R_1 U_{11}}{U_{21}}$$
$$= \frac{-1 \text{ M}\Omega * 200 \text{ V}}{-200 \text{ V}}$$
$$= 1 \text{ M}\Omega$$

While the present disclosure is illustrated and described in detail according to the above embodiments, the present disclosure is not limited to these embodiments and additional embodiments may be implemented. Further, other embodiments and various modifications will be apparent to those skilled in the art from consideration of the specification and practice of one or more embodiments disclosed herein, without departing from the scope of the present disclosure.

LIST OF REFERENCE NUMERALS

101 battery (for example, a high-voltage battery)
102 circuit of battery 101
103 terminal of battery 101
104 terminal of battery 101
109 node
110 circuit for measuring the insulation resistance of battery 101
111 ground
116 terminal of circuit 110
117 terminal of circuit 110
201 to 208 method steps
C1, C2 insulation capacitor
Cm capacitor
R1, R2 insulation resistance
Rm1 resistor
Rm2 resistor
t time

The invention claimed is:

1. A method for determining an insulation variable of an electrical network, comprising:
    measuring a first voltage at the network that drops between a supply terminal of the electrical network and a reference point of the electrical network;
    connecting an auxiliary system to the network between the supply terminal and the reference point;
    measuring, after the auxiliary system is connected, a second voltage that drops between the supply terminal and the reference point;
    disconnecting the auxiliary system from the network;
    measuring, after the auxiliary system is disconnected, a third voltage that drops between the supply terminal and the reference point; and
    determining the insulation variable based on the first voltage, the second voltage, and the third voltage.

2. The method according to claim 1, wherein the insulation variable is one of an insulation capacitance or an insulation resistance.

3. The method according to claim 1, wherein the network is an electrical supply network comprising at least one battery.

4. The method according to claim 1, wherein connecting the auxiliary system to the network comprises closing a switch associated with the auxiliary system.

5. The method according to claim 1, wherein the auxiliary system comprises:
    a capacitor, a first resistor, and a switch connected in series; and
    a second resistor connected in parallel with the capacitor.

6. The method according to claim 1, wherein measuring the second voltage comprises measuring the second voltage when a predefined settling time has passed after the auxiliary system is connected to the network.

7. The method according to claim 1, wherein measuring the third voltage comprises measuring the third voltage when a predefined duration has passed after the auxiliary system is disconnected from the network.

8. The method according to claim 7, wherein determining the insulation variable comprises determining a parallel insulation resistance in accordance with $$RP = \frac{-t1}{CP \cdot \ln\left(1 - \frac{U1(t1) - U12}{U11 - U12}\right)}$$

where $$CP = Cm * \frac{U12}{U11 - U12}$$

wherein
    RP denotes the parallel insulation resistance,
    CP denotes a parallel insulation capacitance,
    U11 denotes the first voltage,
    U12 denotes the second voltage,
    U1(t1) denotes the third voltage,
    t1 denotes the predefined duration, and
    Cm denotes an insulation capacitor of the auxiliary system.

9. The method according to claim 8:
    wherein the supply terminal is a first supply terminal,
    the method further comprising:
        measuring a fourth voltage before the auxiliary system is connected to the network, wherein the fourth voltage is measured between the reference point and a second supply terminal of the network, and
        determining a first insulation resistance of the network between the first supply terminal and the reference point and a second insulation, resistance of the network between the reference point and the second supply terminal, in accordance with $$R1 = RP \cdot \left(1 - \frac{U11}{U21}\right)$$

and $$R2 = \frac{-R1 \cdot U11}{U21}$$

wherein
    R1 denotes the first insulation resistance,
    R2 denotes the second insulation resistance, and
    U21 denotes the fourth voltage.

10. The method according to claim 8, wherein the duration t1 depends on a resolution of an analog-to-digital converter connected to the auxiliary system.

11. A device for determining an insulation variable of an electrical network, comprising:
    an auxiliary system; and
    a processing unit coupled to the auxiliary system, the processing unit configured to perform the following operations:

measuring a first voltage at the network that drops between a supply terminal of the electrical network and a reference point of the electrical network;

connecting the auxiliary system to the network between the supply terminal and the reference point;

measuring, after the auxiliary system is connected, a second voltage that drops between the supply terminal and the reference point;

disconnecting the auxiliary system from the network;

measuring, after the auxiliary system is disconnected, a third voltage that drops between the supply terminal and the reference point; and determining the insulation variable based on the first voltage, the second voltage, and the third voltage.

12. The device according to claim 11, wherein the insulation variable is one of an insulation capacitance or an insulation resistance.

13. The device according to claim 11, wherein the network is an electrical supply network comprising at least one battery.

14. The device according to claim 11, further comprising: a switch configured to connect the auxiliary system to the network.

15. The device according to claim 11, wherein the auxiliary system comprises:

a capacitor, a first resistor, and a switch connected in series; and a second resistor connected in parallel with the capacitor.

16. The device according to claim 11, wherein the processing unit is further configured to measure the second voltage when a predefined settling time has passed after the auxiliary system is connected to the network.

17. The device according to claim 11, wherein the processing unit is further configured to measure the third voltage when a predefined duration has passed after the auxiliary system is disconnected from the network.

18. The device according to claim 11, wherein the processing unit is further configured to measure a parallel insulation resistance as the insulation variable in accordance with $$RP = \frac{-t1}{CP \cdot \ln\left(1 - \frac{U1(t1) - U12}{U11 - U12}\right)}$$

where $$CP = Cm * \frac{U12}{U11 - U12}$$

wherein

RP denotes the parallel insulation resistance,
CP denotes a parallel insulation capacitance,
U11 denotes the first voltage,
U12 denotes the second voltage,
U1(t1) denotes the third voltage,
t1 denotes the predefined duration, and
Cm denotes an insulation capacitor of the auxiliary system.

19. The device according to claim 18, wherein:

the supply terminal is a first supply terminal, and the processing unit is further configured to perform the following operations:

measuring a fourth voltage before the auxiliary system is connected to the network, wherein the fourth voltage is measured between the reference point and a second supply terminal of the network, and determining a first insulation resistance of the network between the first supply terminal and the reference point and a second insulation resistance of the network between the reference point and the second supply terminal, in accordance with $$R1 = RP \cdot \left(1 - \frac{U11}{U21}\right)$$

and $$R2 = \frac{-R1 \cdot U11}{U21}$$

wherein

R1 denotes the first insulation resistance,
R2 denotes the second insulation resistance, and
U21 denotes the fourth voltage.

20. A motor vehicle comprising at least one device according to claim 11.

* * * * *